(12) United States Patent
Komoriya

(10) Patent No.: US 10,849,514 B2
(45) Date of Patent: Dec. 1, 2020

(54) INFORMATION PROCESSING DEVICE AND INFORMATION PROCESSING METHOD

(71) Applicant: SONY CORPORATION, Tokyo (JP)

(72) Inventor: Yota Komoriya, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 240 days.

(21) Appl. No.: 15/575,531

(22) PCT Filed: Mar. 24, 2016

(86) PCT No.: PCT/JP2016/059285
§ 371 (c)(1),
(2) Date: Nov. 20, 2017

(87) PCT Pub. No.: WO2016/194445
PCT Pub. Date: Dec. 8, 2016

(65) Prior Publication Data
US 2018/0132737 A1 May 17, 2018

(30) Foreign Application Priority Data

Jun. 2, 2015 (JP) ................................. 2015-112180

(51) Int. Cl.
*A61B 5/024* (2006.01)
*A61B 5/02* (2006.01)
*A61B 5/00* (2006.01)
*A61B 5/11* (2006.01)

(52) U.S. Cl.
CPC ............ *A61B 5/02427* (2013.01); *A61B 5/02* (2013.01); *A61B 5/7221* (2013.01); *A61B 5/7285* (2013.01); *A61B 5/1112* (2013.01); *A61B 5/1118* (2013.01); *A61B 2560/0242* (2013.01); *A61B 2562/0238* (2013.01)

(58) Field of Classification Search
CPC ............ A61B 5/02427; A61B 5/02416; A61B 5/02433; A61B 5/7285; A61B 5/14552
See application file for complete search history.

(56) References Cited

U.S. PATENT DOCUMENTS 7,468,036 B1 * 12/2008 Rulkov .............. A61B 5/02438
600/485

FOREIGN PATENT DOCUMENTS

| JP | 2011-019973 A | 2/2011 |
| JP | 2011-19973 A | 2/2011 |
| JP | 2011-217784 A | 11/2011 |
| JP | 2013-202289 A | 10/2013 |
| JP | 2014-057717 A | 4/2014 |

OTHER PUBLICATIONS

JP 2011-217784A Machine translation. (Year: 2011).*
International Search Report and Written Opinion of PCT Application No. PCT/JP2016/059285, dated Jun. 21, 2016, 7 pages of ISRWO.

* cited by examiner

*Primary Examiner* — Carrie R Dorna
(74) *Attorney, Agent, or Firm* — Chip Law Group

(57) ABSTRACT

Provided is an information processing device including: a sensor control unit configured to control a light emission intensity of a light source included in a pulse wave sensor on the basis of a state of a user who is a detection target of the pulse wave sensor.

16 Claims, 4 Drawing Sheets

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2016/059285 filed on Mar. 24, 2016, which claims priority benefit of Japanese Patent Application No. JP 2015-112180 filed in the Japan Patent Office on Jun. 2, 2015. Each of the above-referenced applications is hereby incorporated herein by reference in its entirety.

TECHNICAL FIELD

The present disclosure relates to an information processing device and an information processing method.

BACKGROUND ART

Technologies related to beat detection devices reducing power consumption in accordance with determination results or the like of physical activity states have been developed. As a technology related to a beat detection device, a technology disclosed in, for example, the following Patent Literature 1 can be exemplified.

CITATION LIST

Patent Literature

Patent Literature 1: JP 2013-202289A

DISCLOSURE OF INVENTION

Technical Problem

For example, a device using the technology disclosed in Patent Literature 1 changes a sensing frequency of a pulse wave sensor in accordance with a determination result or the like of a physical activity state. There is a possibility of power consumption being by changing the sensing frequency of the pulse wave sensor as in the technology disclosed in Patent Literature 1.

Here, in a case in which a user wearing a device including a pulse wave sensor on his or her body such as on his or her arm, that is, a user who is a detection target of the pulse wave sensor, is moving, there is a concern of an influence of, for example, stray light (for example, light other than detection target light, such as outside light or reflected light reflected from a surface of the user; the same applies below) on the pulse wave sensor due to the motion of the user. However, for example, even when the sensing frequency of the pulse wave sensor is changed as in the technology disclosed in Patent Literature 1, the influence of stray light described above may not be reduced. Accordingly, for example, even when the technology disclosed in Patent Literature 1 is used, a pulse wave may not be obtained stably on the basis of a detection signal of the pulse wave sensor.

The present disclosure proposes a novel and improved information processing device and a novel and improved information processing method capable of achieving compatibility between stable detection of a pulse wave by a pulse wave sensor and a reduction in power consumption in the pulse wave sensor.

Solution to Problem

According to the present disclosure, there is provided an information processing device including: a sensor control unit configured to control a light emission intensity of a light source included in a pulse wave sensor on the basis of a state of a user who is a detection target of the pulse wave sensor.

In addition, according to the present disclosure, there is provided an information processing method performed by an information processing device, including: a step of controlling a light emission intensity of a light source included in a pulse wave sensor on the basis of a state of a user who is a detection target of the pulse wave sensor.

Advantageous Effects of Invention

According to the present disclosure, it is possible to achieve compatibility between stable detection of a pulse wave by the pulse wave sensor and a reduction in power consumption in the pulse wave sensor.

Note that the effects described above are not necessarily limitative. With or in the place of the above effects, there may be achieved any one of the effects described in this specification or other effects that may be grasped from this specification.

MODE FOR CARRYING OUT THE INVENTION

Figure 1:
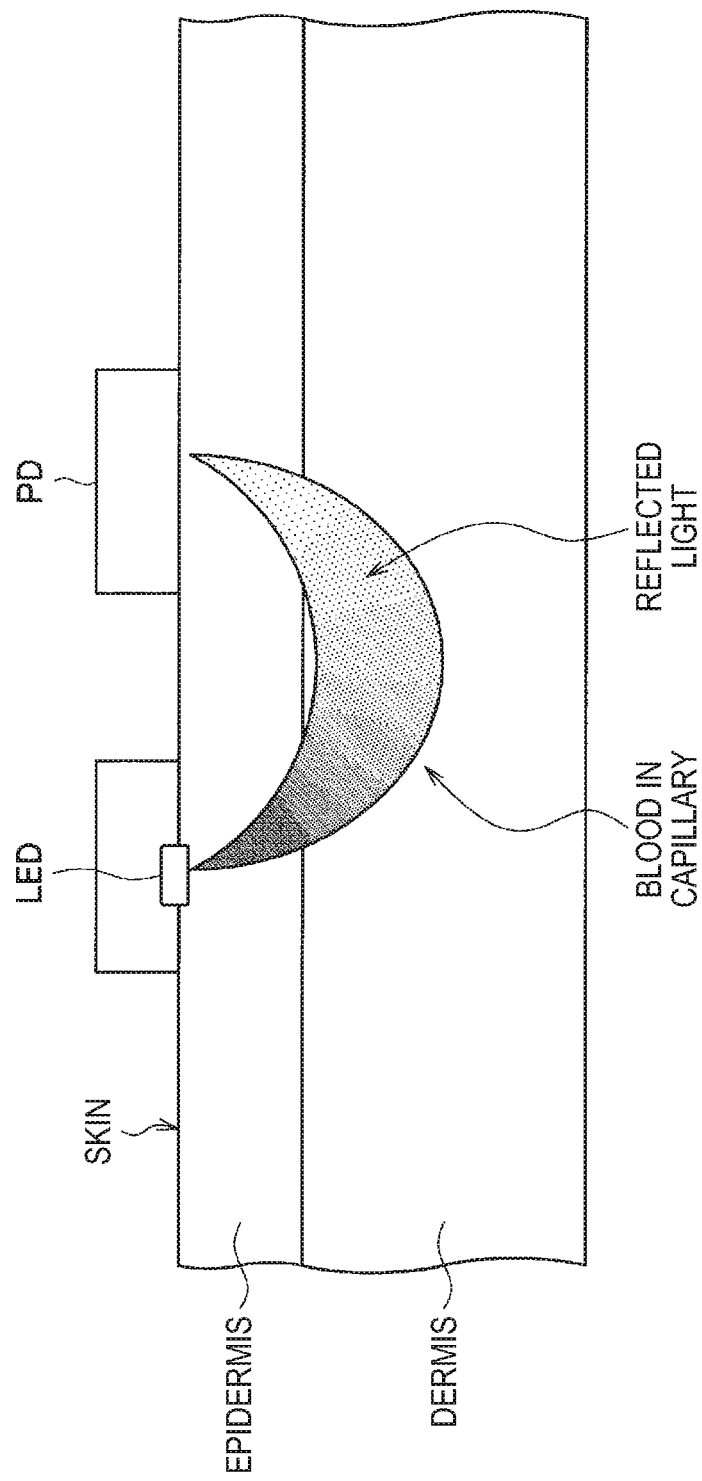
FIG. 1 is an explanatory diagram illustrating an overview of an information processing method according to an embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

In addition, the description will be made in the following order.

1. Information processing method according to embodiment
2. Information processing device according to embodiment
3. Program according to embodiment (Information Processing Method According to Embodiment)

First, an information processing method according to an embodiment will be described. Hereinafter, a case in which a process related to the information processing method according to the embodiment is performed by an information processing device according to the embodiment will be exemplified.

[1] Overview of Information Processing Method According to Embodiment

FIG. 1 is an explanatory diagram illustrating an overview of the information processing method according to the embodiment and illustrates an example of a pulse wave detection method by a pulse wave sensor.

FIG. 1 conceptually illustrates a part of the body of a user who wears the pulse wave sensor on his or her body such as an arm, that is, a user who is a detection target of the pulse wave sensor along with an example of a configuration of the pulse wave sensor. Hereinafter, the user who is a detection target of the pulse wave sensor is simply referred to as a "user" in some cases.

In addition, FIG. 1 illustrates an example of a pulse wave sensor that detects a pulse wave in accordance with a photoelectric pulse wave scheme (PPG (plethysmogram) scheme). In FIG. 1, for convenience, a light-emitting diode (illustrated as "LED" (light-emitting diode) in FIG. 1) which is an example of a light source and a photodiode (illustrated as "PD" (photodiode) in FIG. 1) which is an example of a light-receiving element in the configuration of the pulse wave sensor are illustrated.

Also, the configuration of the pulse wave sensor according to the embodiment is not limited to the example illustrated in FIG. 1.

For example, on the rear stage of the photodiode (which is an example of a light-receiving element; the same applies below) illustrated in FIG. 1, the pulse wave sensor may include one or both of an amplification circuit that amplifies an analog signal output from the photodiode and an analog-to-digital converter (ADC) that converts the analog signal (or the amplified analog signal) into a digital signal. In addition, on the rear stage of the photodiode (which is an example of a light-receiving element; the same applies below) illustrated in FIG. 1, the pulse wave sensor may include a filter circuit used to remove noise included in a detection signal. Here, "photodiode" or "one or two or more of the photodiode, the amplification circuit, the analog-to-digital converter, and the filter circuit" corresponds to a light-receiving device included in the pulse wave sensor.

In addition, an example in which the photodiode included in the pulse wave sensor detects reflected light obtained when light emitted from a light-emitting diode (which is an example of a light source; the same applies below) included in the pulse wave sensor is reflected from a blood vessel is illustrated in FIG. 1. However, the photodiode included in the pulse wave sensor may be configured to detect transmitted light obtained when light emitted from the light-emitting diode included in the pulse wave sensor is transmitted through a blood vessel.

In addition, the configuration in which the light-emitting diode is included as a light source is illustrated in FIG. 1, but the pulse wave sensor according to the embodiment may include any light source capable of spontaneously emitting light or emitting light by reflecting the light.

In addition, the configuration in which the photodiode is included as the light-receiving element is illustrated in FIG. 1, but the pulse wave sensor according to the embodiment may include any element (or circuit) capable of obtaining a signal in accordance with received light as a light-receiving element.

In addition, the configuration in which the pulse wave sensor includes one light-emitting diode and one photodiode is illustrated in FIG. 1, but the pulse wave sensor according to the embodiment may include, for example, a plurality of light-emitting diodes or may include a plurality of photodiodes.

Here, the photoelectric pulse wave scheme is a pulse wave measurement scheme of measuring a change in the capacity of a blood vessel occurring when the heart of a user who is a detection target of the pulse wave sensor discharges blood.

In a case in which the photoelectric pulse wave scheme is used, as illustrated in FIG. 1, the light-emitting diode included in the pulse wave sensor emits light, and the photodiode outputs an analog signal in accordance with reflected light (or transmitted light) received via skin, a blood vessel, or the like of the user. Here, the analog signal output from the photodiode is changed in accordance with a change in the amount of received light due to an increase or decrease in an amount of blood in association with beats of the heart.

Accordingly, in a case in which the photoelectric pulse wave scheme is used, a pulse wave is detected in accordance with a detection signal (an analog signal or a digital signal) based on an analog signal output from the photodiode.

As described above, in a case in which the user wearing the pulse wave sensor (or a device including the pulse wave sensor) on his or her body such as on his or her arm is moving, there is a concern of an influence of, for example, stray light on the pulse wave sensor due to the motion of the user.

As a specific example, an amount of stray light (hereinafter referred to as a "stray light amount") incident on the photodiode is changed due to an influence of "a change in a wearing state of the pulse wave sensor in association with the motion of the user" or "a shadow occurring when the light source is shielded with the motion of the user."

In a case in which the photoelectric pulse wave scheme is used, a signal component of a pulse wave included in the amount of light received by the photodiode of the pulse wave sensor is very small. As a specific example, in a case in which the pulse wave sensor is worn on a finger of the user, a signal component of a pulse wave included in the amount of light received by the photodiode of the pulse wave sensor is about 3 to 5 [%]. In addition, in a case in which the pulse wave sensor is worn on a wrist of the user, a signal component of a pulse wave included in the amount of light received by the photodiode of the pulse wave sensor is about 1 to 2 [%]. That is, most of the signal component of the pulse wave included in the amount of light received by the photodiode of the pulse wave sensor is a so-called direct current (DC) component. An alternating current (AC) component indicating a change in the amount of received light due to an increase or decrease in an amount of blood in association with beats of the heart of the user can be said to be considerably smaller than the DC component.

Here, the change in the amount of stray light is represented as degradation of a signal-to-noise ratio (S/N ratio) of the detection signal of the pulse wave sensor or a peak of a pseudo-pulse wave. When the amount of stray light increases, a DC component of the detection signal increases. As a result, an AC component indicating a pulse wave is buried in a change in the DC component. Accordingly, in a case in which the amount of stray amount is changed, a peak of the AC component is not seen. Therefore, for example, it is difficult to detect the position of the peak of the pulse wave from the detection signal, and thus there is a concern of detection precision of the pulse wave deteriorating.

As a method of improving a signal property of the detection signal due to the change in the amount of stray light described above, for example, a method of increasing an amount of light emitted from the light source to improve the light emission intensity can be exemplified.

Since the amplitude of the AC component in the detection signal can be set to be larger by raising the light emission intensity, it is possible to further increase the signal component of the pulse wave in accordance with the increase or decrease in the amount of blood in association with beats of the heart. Accordingly, by using the method of raising the light emission intensity, it is possible to achieve stable detection of the pulse wave by the pulse wave sensor.

However, in a case in which the light emission intensity is simply raised, power consumption by the light source increases. Therefore, power consumption of the pulse wave sensor increases.

Here, for example, the pulse wave sensor can be included in a wearable device worn on the body of the user for use. Examples of the wearable device according to the embodiment include "devices worn on parts of the user's body such as the hands, arms, neck, and legs, such as watch type devices or accessory type devices such as rings, bracelets, necklaces, and nail type devices," "glasses type devices," and "clothing, shoe, sock, and hat type devices."

In the foregoing wearable device, the size of a mountable battery is restricted due to the size of the device or the like and there are many requests for increasing a driving time since the device is worn on the body for use. Therefore, in the foregoing wearable device, it is desirable to further reduce power consumption.

As described above, in a case in which the light emission intensity is simply raised, power consumption of the pulse wave sensor increases. Accordingly, in the case in which the light emission intensity is simply raised, it can be said that it is difficult to achieve a reduction in the power consumption.

Accordingly, the information processing device according to the embodiment achieves compatibility between stable detection of a pulse wave by the pulse wave sensor and a reduction in power consumption in the pulse wave sensor by performing, for example, a sensor control process of controlling the pulse wave sensor on the basis of a state of a user who is a detection target of the pulse wave sensor as the process related to the information processing method according to the embodiment.

Here, as the state of the user according to the embodiment, for example, "asleep," "physically active (hereinafter referred to as 'exercising' in some cases)," and "daily activities (a state other than sleep and physical activity)" can be exemplified.

For example, the state of the user who is a detection target according to the embodiment is estimated on the basis of one or both of "a behavior taken by the user and estimated from a motion of the user, a place (location) where the user is located, a behavior history of the user, or the like" and "an environment in which the user is located and which is estimated from a sensing result or the like of a sensor related to sensing of an environment of an illuminance sensor, a microphone, or the like."

The process related to the estimation of the state of the user who is the detection target may be performed by the information processing device according to the embodiment or may be performed by an external device of the information processing device according to the embodiment. In a case in which the process related to the estimation of the state of the user who is the detection target is performed by the external device, the information processing device according to the embodiment controls the pulse wave sensor on the basis of an estimation result of the state of the user in the external device.

Also, a method of estimating the state of the user according to the embodiment is not limited to the example described above.

For example, the state of the user according to the embodiment may be estimated on the basis of a detection result based on a detection signal of the pulse wave sensor. As the detection result based on the detection signal of the pulse wave sensor, for example, a pulse rate during a predetermined period, a change in the pulse rate, an amplitude value of the detection signal of the pulse wave sensor during the predetermined period, and a change in the amplitude value can be exemplified.

That is, the information processing device according to the embodiment can also control the pulse wave sensor through feedback control in which the detection signal of the pulse wave sensor which is a control target of the sensor control process is used.

In addition, examples of the state of the user according to the embodiment are not limited to the examples described above.

For example, as the state of the user according to the embodiment, any state which relates to the user and can be estimated on the basis of one or two or more of a behavior taken by the user, an environment in which the user is located, and a detection result based on the detection signal of the pulse wave sensor, such as a "walking state," a "running state," and a "vehicle riding state" can be exemplified.

Hereinafter, a case in which the state of the user who is the detection target according to the embodiment is estimated on the basis of one or both of a behavior taken by the user and an environment in which the user is located will be mainly exemplified.

More specifically, the information processing device according to the embodiment achieves compatibility between the stable detection of a pulse wave by the pulse wave sensor and the reduction in the power consumption in the pulse wave sensor, for example, by controlling the pulse wave sensor on the basis of the state of the user and realizing the following (A) and (B).

(A) Stable Detection of Pulse Wave by Pulse Wave Sensor

For example, the information processing device according to the embodiment raises the light emission intensity to correspond to the state of the user estimated on the basis of one or both of a behavior taken by the user and an environment in which the user is located. The information processing device according to the embodiment raises the light emission intensity, for example, by increasing the amount of light emitted from the light source of the pulse wave sensor more than an amount of emitted light serving as a reference to correspond to the state of the user.

By increasing the amount of light emitted from the light source of the pulse wave sensor and raising the light emission intensity, it is possible to increase a signal component (for example, an AC component) effective in detection of a pulse wave and included in the detection signal of the pulse wave sensor.

In addition, the signal component effective in detection of a pulse wave increases due to an increase in the amount of light emitted from the light source of the pulse wave sensor, and thus an influence of the DC component of the detection signal which may be noise in the detection of the pulse wave relatively decreases. That is, countermeasures for the noise related to the detection of the pulse wave are realized by increasing the amount of light emitted from the light source of the pulse wave sensor and raising the light emission intensity.

Accordingly, the information processing device according to the embodiment can realize the stable detection of a pulse wave by the pulse wave sensor by increasing the amount of light emitted from the light source of the pulse wave sensor and raising the light emission intensity.

Also, the process related to the detection of the pulse wave based on the detection signal of the pulse wave sensor may be performed by the information processing device according to the embodiment or may be performed by an external device of the information processing device according to the embodiment.

(B) Reduction in Power Consumption in Pulse Wave Sensor

For example, the information processing device according to the embodiment controls the light emission intensity of the light source of the pulse wave sensor on the basis of the state of the user estimated on the basis of one or both of a behavior taken by the user and an environment in which the user is located.

For example, the information processing device according to the embodiment restricts a period in which the amount of light emitted from the light source of the pulse wave sensor related to the foregoing (A) is increased, that is, a period in which the light emission intensity is raised, on the basis of the estimated state of the user.

By restricting the period in which the light emission intensity of the pulse wave sensor is raised on the basis of the state of the user, it is possible to reduce power consumption in the pulse wave sensor in a case in which a pulse wave can be stably detected even when the light emission intensity is not raised. In addition, by reducing the power consumption in the pulse wave sensor in a case in which a pulse wave can be stably detected even when the light emission intensity is not raised, it is possible to avoid wasting unnecessarily consumed power in the pulse wave sensor. Accordingly, by restricting the period in which the light emission intensity is raised, the information processing device according to the embodiment can further reduce the power consumption in the pulse wave sensor than in a case in which the above-described method of simply raising the light emission intensity is used.

In addition, for example, the information processing device according to the embodiment lowers the light emission intensity of the light source of the pulse wave sensor on the basis of the estimated state of the user. The information processing device according to the embodiment lowers the light emission intensity, for example, by lowering an amount of light emitted from the light source of the pulse wave sensor further than an amount of emitted light serving as a reference to correspond to the state of the user.

The information processing device according to the embodiment achieves compatibility between the stable detection of a pulse wave by the pulse wave sensor and the reduction in the power consumption in the pulse wave sensor by controlling the pulse wave sensor on the basis of the state of the user and realizing the foregoing (A) and (B).

In addition, as described above, for example, the pulse wave sensor can be included in a wearable device worn on the body of the user for use. Here, in a case in which the state of the user is estimated on the basis of a sensing result of a sensor capable of detecting a motion of the user, such as an acceleration sensor or a gyro sensor included in the wearable device, when the pulse wave sensor is included in the wearable device, power is consumed in the sensor when the light emission intensity is controlled in the wearable device. However, average power consumption of the sensor is, for example, about 1/1000 to 1/10 of power consumption at the time of light emission of a light-emitting diode, and thus is less than power consumption at the time of light emission of the light-emitting diode.

Accordingly, in a case in which it is necessary to drive the sensor included in the wearable device including the pulse wave sensor when the state of the user is estimated as described above, it is possible to achieve the reduction in the power consumption in the entire wearable device even when the light emission intensity of the light source of the pulse wave sensor is controlled.

Hereinafter, the process related to the information processing method according to the embodiment will be described more specifically.

[2] Process Related to Information Processing Method According to Embodiment (1) Sensor Control Process The information processing device according to the embodiment controls the light emission intensity of the light source included in the pulse wave sensor on the basis of the state of the user who is a detection target of the pulse wave sensor.

Here, the number of light sources included in the pulse wave sensor may be singular or plural.

For example, in a case in which the pulse wave sensor includes one light-emitting diode as the light source, the information processing device according to the embodiment controls a current flowing in the one light-emitting diode to control an amount of light emitted from the light-emitting diode and controls the light emission intensity of the light-emitting diode included in the pulse wave sensor.

In a case in which the information processing device according to the embodiment includes the pulse wave sensor, the information processing device according to the embodiment controls the light emission intensity of the light-emitting diode included in the pulse wave sensor, for example, by controlling a switch transistor electrically connected to the light-emitting diode such that the switch transistor is turned on and off.

In addition, in a case in which a device including the pulse wave sensor (for example, a wearable device) is an external device of the information processing device according to the embodiment, the information processing device according to the embodiment controls the light emission intensity of the light-emitting diode included in the pulse wave sensor, for example, by transmitting a control signal including a command for controlling light emission of the light-emitting diode to the external device. The information processing device according to the embodiment transmits the control signal to the external device via, for example, a communication unit (to be described below) included in the information processing device according to the embodiment or an external communication device connected to the information processing device according to the embodiment.

Here, as the control of the light emission intensity of the light source such as a light-emitting diode, for example, pulse width modulation (PWM) control can be exemplified. In addition, the control of the light emission intensity of the light source such as the light-emitting diode may be control of a light emission level of the light source in a case in which the light source normally emits light.

Also, a method of controlling the light emission intensity of the light-emitting diode included in the pulse wave sensor according to the embodiment is not limited to the foregoing method. The information processing device according to the embodiment can control the light emission intensity of the light-emitting diode included in the pulse wave sensor, for example, in accordance with any method capable of controlling the light emission intensity of the light-emitting diode included in the pulse wave sensor.

In addition, for example, in a case in which the pulse wave sensor includes the plurality of light-emitting diodes as the plurality of light sources, the information processing device according to the embodiment controls the light emission intensity of each of the plurality of light-emitting diodes.

Here, colors of light emitted from the plurality of light sources included in the pulse wave sensor may be the same color or may be different colors.

When the colors of the light emitted from the plurality of light sources included in the pulse wave sensor are the same color, the light emission intensity of each of the light sources included in the pulse wave sensor is controlled by the information processing device according to the embodiment, and thus the light emission intensity of the light of one color emitted from the light source included in the pulse wave sensor is controlled.

In addition, in a case in which there are the plurality of colors of light emitted from the plurality of light sources included in the pulse wave sensor, the light emission intensity of each of the light sources included in the pulse wave sensor is controlled by the information processing device according to the embodiment, and thus the light emission intensity of the light of each of the plurality of colors emitted from the light sources included in the pulse wave sensor is controlled.

Through the control of the light emission intensity of the light of each of the plurality of colors emitted from the light sources included in the pulse wave sensor in the information processing device according to the embodiment, for example, a detection signal can be obtained with light obtained by combining the light of the different colors in the pulse wave sensor.

In addition, for example, setting the amount of emitted light of one or two or more colors to 0 (zero) among the light of the plurality of colors, that is, emitting no light from one or two or more light sources among the plurality of light sources included in the pulse wave sensor, may be included in the control of the light emission intensity of the light of each of the plurality of colors emitted from the light sources included in the pulse wave sensor in the information processing device according to the embodiment.

By emitting no light from one or two or more light sources among the plurality of light sources included in the pulse wave sensor, for example, it is possible to realize emitting light from only the light sources that emit light of specific colors among the plurality of light sources included in the pulse wave sensor. By emitting light from only the light source that emits light of a specific color among the plurality of light sources included in the pulse wave sensor, for example, a detection signal can be obtained with the light of one color among the plurality of colors of the light in the pulse wave sensor.

For example, the information processing device according to the embodiment can realize switching between the colors of the light emitted from the plurality of light sources included in the pulse wave sensor by controlling the light intensity of the light of each of the plurality of colors emitted from the light sources included in the pulse wave sensor. Here, for example, in a case in which a pulse wave may not be detected on the basis of a detection result of the pulse wave based on the detection signal in the light of one color, the information processing device according to the embodiment switches the colors of the light emitted from the plurality of light sources included in the pulse wave sensor to other colors. In addition, for example, the information processing device according to the embodiment may switch the colors of the light emitted from the plurality of light sources included in the pulse wave sensor to colors of the light corresponding to a use purpose for each detection purpose (for example, detection of a blood oxygen concentration or detection of other blood components). In addition, for example, in order to reduce noise and improve detection precision of a pulse wave, the information processing device according to the embodiment can also switch the colors of the light emitted from the plurality of light sources included in the pulse wave sensor in sequence.

Hereinafter, a process related to the control of the light emission intensity of the light source included in the pulse wave sensor will be described more specifically.

The information processing device according to the embodiment performs processes described in, for example, the following (1-1) to (1-3) as the sensor control process.

(1-1) First Example of Sensor Control Process

The information processing device according to the embodiment controls the light emission intensity of the light source included in the pulse wave sensor on the basis of a variation amount of the light emission intensity corresponding to the state of the user and a comparison result of an amplitude value of the detection signal of the pulse wave sensor and a predetermined threshold.

For example, the information processing device according to the embodiment specifies the variation amount of the light emission intensity corresponding to the estimated state of the user by referring to a table (or a database) in which the state of the user is associated with the variation amount of the light emission intensity. Also, a method of specifying the variation amount of the light emission intensity corresponding to the state of the user is not limited to the above-described example. The information processing device according to the embodiment may use any method as long as the variation amount of the light emission intensity corresponding to the estimated state of the user can be specified.

Here, as the variation amount of the light emission intensity according to the embodiment, for example, a value for directly regulating a variation in the amount of light emitted from the light-emitting diode included in the pulse wave sensor (for example, the variation amount of the amount of emitted light) or a value for indirectly regulating the variation amount of the amount of emitted light (for example, a value associated with the variation amount of the amount of emitted light) can be exemplified.

In a case in which the variation amount of the light emission intensity according to the embodiment is the value for directly regulating the variation in the amount of emitted light of the light-emitting diode included in the pulse wave sensor, the information processing device according to the embodiment controls the light emission intensity of the light source included in the pulse wave sensor such that the amount of light emitted from the light-emitting diode is varied by that value.

In addition, in a case in which the variation amount of the light emission intensity according to the embodiment is the value for indirectly regulating the variation in the amount of light emitted from the light-emitting diode included in the pulse wave sensor, the information processing device according to the embodiment specifies the variation amount of the amount of emitted light corresponding to the variation amount of the light emission intensity, for example, using the table (or the database) in which the value for indirectly regulating the variation in the amount of emitted light is associated with the variation amount of the amount of emitted light. Then, the information processing device according to the embodiment controls the light emission intensity of the light source included in the pulse wave sensor such that the amount of light emitted from the light-emitting diode is varied by the specified variation amount of the amount of emitted light.

The predetermined threshold in the sensor control process related to the first example is a threshold used in threshold processing with the amplitude value of the detection signal of the pulse wave sensor. As the predetermined threshold in the sensor control process related to the first example, for example, a fixed threshold which is set in advance or a variable threshold which can be set on the basis of a user manipulation can be exemplified.

Hereinafter, the sensor control process related to the first example will be described more specifically.

For example, in a case in which the amplitude value of the detection signal of the pulse wave sensor is greater than the predetermined threshold, the information processing device according to the embodiment controls the light emission intensity of the light source included in the pulse wave sensor on the basis of the variation amount of the light emission intensity corresponding to the state of the user such that the light emission intensity decreases. In addition, for example, in a case in which the amplitude value of the detection signal of the pulse wave sensor is equal to or less than the predetermined threshold, the information processing device according to the embodiment controls the light emission intensity of the light source included in the pulse wave sensor on the basis of the variation amount of the light emission intensity corresponding to the state of the user such that the light emission intensity increases.

Here, for example, the information processing device according to the embodiment controls the light emission intensity of the light source included in the pulse wave sensor such that a manner of changing the light emission intensity in the case in which the light emission intensity decreases is identical to a manner of changing the light emission intensity in the case in which the light emission intensity increases. As the identicalness between the manners of changing the light emission intensity according to the embodiment, for example, identicalness between speeds at which the light emission intensity is changed (for example, periods necessary until the light emission intensity is varied by the variation amount of the light emission intensity are the same), can be exemplified.

In addition, for example, the information processing device according to the embodiment controls the light emission intensity of the light source included in the pulse wave sensor such that the manner of changing the light emission intensity in the case in which the light emission intensity decreases is different from the manner of changing the light emission intensity in the case in which the light emission intensity increases. As the differences between the manners of changing the light emission intensity according to the embodiment are different, for example, a difference in a speed at which the light emission intensity is changed (for example, switching between periods necessary until the light emission intensity is varied by the variation amount of the light emission intensity in a case in which the light emission intensity increases and a case in which the light emission intensity decreases), can be exemplified.

Also, the sensor control process related to the first example is not limited to the above-described example.

For example, in a case in which the amplitude value of the detection signal of the pulse wave sensor is equal to or greater than the predetermined threshold, the information processing device according to the embodiment may control the light emission intensity of the light source included in the pulse wave sensor on the basis of the variation amount of the light emission intensity corresponding to the state of the user such that the light emission intensity decreases. In addition, for example, in a case in which the amplitude value of the detection signal of the pulse wave sensor is less than the predetermined threshold, the information processing device according to the embodiment may control the light emission intensity of the light source included in the pulse wave sensor on the basis of the variation amount of the light emission intensity corresponding to the state of the user such that the light emission intensity increases.

(1-2) Second Example of Sensor Control Process

The information processing device according to the embodiment controls the light emission intensity of the light source of the light source included in the pulse wave sensor on the basis of a predetermined variation amount of the light emission intensity and a comparison result of the amplitude value of the detection signal of the pulse wave sensor and a threshold corresponding to the state of the user.

As the predetermined variation amount of the light emission intensity in the sensor control process related to the second example, for example, a fixed variation amount which is set in advance or a variable variation amount which can be set on the basis of a user manipulation can be exemplified.

In addition, the threshold in the sensor control process related to the second example is a threshold used in threshold processing with the amplitude value of the detection signal of the pulse wave sensor. The information processing device according to the embodiment specifies a threshold corresponding to the estimated state of the user, for example, by referring to a table (or a database) in which the state of the user is associated with the threshold. Also, a method of specifying the threshold corresponding to the state of the user is not limited to the above-described example. The information processing device according to the embodiment may also use any method as long as the threshold corresponding to the estimated state of the user can be specified.

Hereinafter, the sensor control process related to the second example will be described more specifically.

For example, in a case in which the amplitude value of the detection signal of the pulse wave sensor is greater than the threshold corresponding to the state of the user, the information processing device according to the embodiment controls the light emission intensity of the light source included in the pulse wave sensor on the basis of the predetermined variation amount of the light emission intensity such that the light emission intensity decreases. In addition, for example, in a case in which the amplitude value of the detection signal of the pulse wave sensor is equal to or less than the threshold corresponding to the state of the user, the information processing device according to the embodiment controls the light emission intensity of the light source included in the pulse wave sensor on the basis of the predetermined variation amount of the light emission intensity such that the light emission intensity increases.

Here, as in the case in which the sensor control process related to the first example is performed, for example, the information processing device according to the embodiment controls the light emission intensity of the light source included in the pulse wave sensor such that a manner of changing the light emission intensity in the case in which the light emission intensity decreases is identical to a manner of changing the light emission intensity in the case in which the light emission intensity increases. In addition, as in the case in which the sensor control process related to the first example is performed, for example, the information processing device according to the embodiment may control the light emission intensity of the light source included in the pulse wave sensor such that the manner of changing the light emission intensity in the case in which the light emission intensity decreases is different from the manner of changing the light emission intensity in the case in which the light emission intensity increases.

Also, the sensor control process related to the second example is not limited to the above-described example.

For example, in a case in which the amplitude value of the detection signal of the pulse wave sensor is equal to or greater than the threshold corresponding to the state of the user, the information processing device according to the embodiment may control the light emission intensity of the light source included in the pulse wave sensor on the basis of the predetermined variation amount of the light emission intensity such that the light emission intensity decreases. In addition, for example, in a case in which the amplitude value of the detection signal of the pulse wave sensor is less than the threshold corresponding to the state of the user, the information processing device according to the embodiment may control the light emission intensity of the light source included in the pulse wave sensor on the basis of the predetermined variation amount of the light emission intensity such that the light emission intensity increases.

(1-3) Third Example of Sensor Control Process

The information processing device according to the embodiment controls the light emission intensity of the light source of the light source included in the pulse wave sensor on the basis of a variation amount of the light emission intensity corresponding to the state of the user and a comparison result of the amplitude value of the detection signal of the pulse wave sensor and a threshold corresponding to the state of the user.

The information processing device according to the embodiment specifies a variation amount of the light emission intensity corresponding to the estimated state of the user, for example, by referring to a table (or a database) in which the state of the user is associated with variation amount of the light emission intensity, as in the case in which the sensor control process related to the first example is performed.

In addition, the threshold in the sensor control process related to the third example is a threshold used in threshold processing with the amplitude value of the detection signal of the pulse wave sensor. As in the case in which the sensor control process related to the second example is performed, the information processing device according to the embodiment specifies the threshold corresponding to the estimated state of the user, for example, by referring to the table (or the database) in which the state of the user is associated with the threshold.

Hereinafter, the sensor control process related to the third example will be described more specifically.

For example, in a case in which the amplitude value of the detection signal of the pulse wave sensor is greater than the threshold corresponding to the state of the user, the information processing device according to the embodiment controls the light emission intensity of the light source included in the pulse wave sensor on the basis of the variation amount of the light emission intensity corresponding to the state of the user such that the light emission intensity decreases. In addition, for example, in a case in which the amplitude value of the detection signal of the pulse wave sensor is equal to or less than the threshold corresponding to the state of the user, the information processing device according to the embodiment controls the light emission intensity of the light source included in the pulse wave sensor on the basis of the variation amount of the light emission intensity corresponding to the state of the user such that the light emission intensity increases.

Here, as in the case in which the sensor control process related to the first example is performed, for example, the information processing device according to the embodiment controls the light emission intensity of the light source included in the pulse wave sensor such that a manner of changing the light emission intensity in the case in which the light emission intensity decreases is identical to a manner of changing the light emission intensity in the case in which the light emission intensity increases. In addition, as in the case in which the sensor control process related to the first example is performed, for example, the information processing device according to the embodiment may control the light emission intensity of the light source included in the pulse wave sensor such that the manner of changing the light emission intensity in the case in which the light emission intensity decreases is different from the manner of changing the light emission intensity in the case in which the light emission intensity increases.

Also, the sensor control process related to the third example is not limited to the above-described example.

For example, in a case in which the amplitude value of the detection signal of the pulse wave sensor is equal to or greater than the threshold corresponding to the state of the user, the information processing device according to the embodiment may control the light emission intensity of the light source included in the pulse wave sensor on the basis of the variation amount of the light emission intensity corresponding to the state of the user such that the light emission intensity decreases. In addition, for example, in a case in which the amplitude value of the detection signal of the pulse wave sensor is less than the threshold corresponding to the state of the user, the information processing device according to the embodiment may control the light emission intensity of the light source included in the pulse wave sensor on the basis of the variation amount of the light emission intensity corresponding to the state of the user such that the light emission intensity increases.

The information processing device according to the embodiment performs the sensor control process described in, for example, the foregoing (1-1) to (1-3) as the process related to the information processing method according to the embodiment.

By performing the sensor control process described in the foregoing (1-1) to (1-3), the light emission intensity of the light source included in the pulse wave sensor is controlled on the basis of the state of the user who is the detection target of the pulse wave sensor. Accordingly, the information processing device according to the embodiment can realize the foregoing (A) and (B) by performing the sensor control process described in, for example, the foregoing (1-1) to (1-3) as the process related to the information processing method according to the embodiment.

Accordingly, the information processing device according to the embodiment can achieve compatibility between the stable detection of a pulse wave by the pulse wave sensor and the reduction in the power consumption in the pulse wave sensor by performing the sensor control process described in, for example, the foregoing (1-1) to (1-3) as the process related to the information processing method according to the embodiment.

Also, the sensor control process according to the embodiment is not limited to the process of controlling the light emission intensity of the light source included in the pulse wave sensor, as described in the foregoing (1-1) to (1-3).

For example, the information processing device according to the embodiment can also further control a light reception operation in the light-receiving device included in the pulse wave sensor as the sensor control process.

In a case in which the information processing device according to the embodiment includes the pulse wave sensor, the information processing device according to the embodiment controls the light reception operation in the light-receiving device by operating the light-receiving device included in the pulse wave sensor in conjunction with light emission of the light source included in the pulse wave sensor.

In addition, in a case in which a device (for example, a wearable device) including the pulse wave sensor is an external device of the information processing device according to the embodiment, the information processing device according to the embodiment controls the light reception operation in the light-receiving device by transmitting a control signal including a command for controlling light emission of an optical diode and a command for controlling the light reception operation in the light-receiving device to the external device.

An example of control of the light reception operation of the light-receiving device will be described exemplifying a case in which the light-receiving device included in the pulse wave sensor includes a photodiode, an amplification circuit, and an analog-to-digital converter.

For example, in a case in which the light emission of the light source is controlled through PWM control, the information processing device according to the embodiment operates one or both of the amplification circuit and the analog-to-digital converter as follows:

the analog-to-digital converter is operated at a timing at which the light source is caused to emit light; and the amplification circuit is operated before the light source is caused to emit light and the light source is caused to emit light at a timing at which the light emission is stopped.

For example, the information processing device according to the embodiment controls the light reception operation of the light-receiving device as described above, and thus power consumption related to the light reception operation in the light-receiving device included in the pulse wave sensor is reduced. Accordingly, the information processing device according to the embodiment achieve the reduction in the power consumption in the entire device including the pulse wave sensor such as a wearable device including the pulse wave sensor, for example, by controlling the light reception operation of the light-receiving device, as described above.

Also, the process related to the information processing method according to the embodiment is not limited to the process (the sensor control process) of the foregoing (1). For example, the information processing device according to the embodiment can also perform one or both of (2) an estimation process and (3) a process based on the detection signal of the pulse wave sensor, as will be described below, as the process related to the information processing method according to the embodiment.

(2) Estimation Process

The information processing device according to the embodiment estimates the state of the user.

For example, the information processing device according to the embodiment estimates the state of the user on the basis of one or two or more of "a behavior taken by the user," "an environment in which the user is located," and "a detection result based on the detection signal of the pulse wave sensor."

Here, "the behavior taken by the user" is estimated, for example, using one or two or more of "a motion of the user estimated in accordance with a sensing result of a sensor capable of detecting the motion of the user, such as an acceleration sensor or a gyro sensor," "a location obtained from a position specifying device capable of specifying a position, such as a Global Positioning System (GPS) device or a place where the user is located and which is estimated from a captured image captured by an imaging device," and "a behavior history of the user based on data indicating a behavior history of the user." For example, whether the user is executing a physical activity can be estimated through "threshold processing in which a sensing result of a sensor capable of detecting a motion of the user is used" or "a combination of a place where the user is located and a behavior history of the user."

The sensor, the position specifying device, or the imaging device is included in, for example, a device including the pulse wave sensor such as a wearable device including the pulse wave sensor. In addition, the sensor, the position specifying device, or the imaging device may be, for example, an external device connected to the device including the pulse wave sensor.

Also, "the behavior taken by the user" may be estimated using any technology capable of estimating a behavior of the user.

In addition, "the environment in which the user is located" is estimated, for example, using, a sensing result of the sensor related to sensing of an environment of an illuminance sensor, a microphone, or the like. For example, whether the user is located in a dark place or a bright place can be estimated through threshold processing in which the sensing result of the illuminance sensor is used.

The sensor related to the sensing of the environment is included in a device including the pulse wave sensor, such as a wearable device including the pulse wave sensor. In addition, the sensor related to the sensing of the environment may be, for example, an external device connected to a device including the pulse wave sensor.

Also, "the environment in which the user is located" may be estimated using any technology capable of estimating the environment in which the user is located.

In addition, for example, "the detection result based on the detection signal of the pulse wave sensor" is obtained on the basis of the detection signal of the pulse wave sensor. For example, as a detection result based on the detection signal of the pulse wave sensor, a pulse rate for a predetermined period, a change in the pulse rate, an amplitude value of the detection signal of the pulse wave sensor for the predetermined period, or a change in the amplitude value can be exemplified. Here, the predetermined period may be a fixed period which is set in advance (for example, 30 seconds or 1 minute) or may be a variable period which can be changed through a user manipulation or the like.

Also, "the detection result based on the detection signal of the pulse wave sensor" is not limited to the foregoing detection result and may be any detection result which can be detected on the basis of the detection signal of the pulse wave sensor.

The information processing device according to the embodiment estimates the state of the user on the basis of one or two or more of "the behavior taken by the user," "the environment in which the user is located," and "the detection result based on the detection signal of the pulse wave sensor" estimated as described above, for example.

For example, in a case in which "the behavior taken by the user" indicates that the user is executing a physical activity, the information processing device according to the embodiment estimates that the state of the user is "physically active." In addition, the information processing device according to the embodiment can also estimate that the state of the user is "physically active," for example, in a case in which a state in which the pulse rate for the predetermined period is greater than a set threshold and which is "the detection result based on the detection signal of the pulse wave sensor" is set continuously continues for a plurality of set periods. In addition, the information processing device according to the embodiment can also estimate that the state of the user is "physically active," for example, in a case in which "the behavior taken by the user" indicates that the user is executing a physical activity and the state in which the pulse rate for the predetermined period is greater than a set threshold and which is "the detection result based on the detection signal of the pulse wave sensor" continuously continues for a plurality of set periods.

In addition, the information processing device according to the embodiment estimates that the state of the user is "asleep," for example, in a case in which "the behavior taken by the user" does not indicate that the user is executing a physical activity and "the environment in which the user is located" indicates that the user is located in a dark place. The information processing device according to the embodiment can also estimate that the state of the user is "asleep," for example, in the case in which "the behavior taken by the user" does not indicate that the user is executing a physical activity and "the environment in which the user is located" indicates that the user is located in a dark place. In addition, the information processing device according to the embodiment can also estimate that the state of the user is "asleep," for example, in a case in which "the behavior taken by the user" does not indicate that the user is executing a physical activity and a state in which the amplitude value of the detection signal of the pulse wave sensor for a predetermined period is less than a set threshold and which is "the detection result based on the detection signal of the pulse wave sensor" continuously continues for a plurality of set periods.

Also, an estimation process according to the embodiment is not limited to the foregoing estimation process. The information processing device according to the embodiment can estimate the state of the user, for example, using any technology capable of estimating the state of the user.

In a case in which the foregoing estimation process is performed, the information processing device according to the embodiment performs the process (the sensor control process) of the foregoing (1) on the basis of the state of the user estimated through the estimation process. Also, even in a case in which the foregoing estimation process is performed, it is needless to say that the information processing device according to the embodiment can perform the process (the sensor control process) of the foregoing (1) on the basis of the state of the user estimated in an external device.

(3) Process Based on Detection Signal of Pulse Wave Sensor

The information processing device according to the embodiment performs the process based on the detection signal of the pulse wave sensor.

As the process based on the detection signal of the pulse wave sensor, for example, a process of obtaining "the detection result based on the detection signal of the pulse wave sensor" on the basis of the detection signal of the pulse wave sensor can be exemplified.

The information processing device according to the embodiment performs a process of acquiring a pulse rate for each set predetermined period as the process of obtaining "the detection result based on the detection signal of the pulse wave sensor." Here, for example, the information processing device according to the embodiment acquires the pulse rate from peak positions of the amplitude of the detection signal. Specifically, for example, the information processing device according to the embodiment may acquire a pulse rate by counting the number of peaks for a predetermined period (for example, 1 [minute]) or may acquire a pulse rate by setting a reciprocal of a time between the peak positions of the amplitude of the detection signal as an instantaneous heart rate. In addition, for example, the information processing device according to the embodiment can also set a moving average of instantaneous heart rates in a time direction as a pulse rate.

In addition, for example, the information processing device according to the embodiment can also acquire a change in a pulse rate for each predetermined period, an amplitude value of the detection signal for each predetermined period, a change in the amplitude value as "the detection result based on the detection signal of the pulse wave sensor."

Also, the process based on the detection signal of the pulse wave sensor according to the embodiment is not limited to the foregoing process.

For example, the information processing device according to the embodiment may perform a process of transmitting data representing "the detection result based on the detection signal of the pulse wave sensor" to an external device such as a server, a process of recording the data representing "the detection result based on the detection signal of the pulse wave sensor" on a recording medium, or a process of notifying of "the detection result based on the detection signal of the pulse wave sensor."

In a case in which the transmission process is performed, the information processing device according to the embodiment transmits the data representing "the detection result based on the detection signal of the pulse wave sensor" to an external device such as a server, for example, by controlling communication of a communication unit (to be described below) or an external communication device connected to the information processing device according to the embodiment. In addition, in a case in which the recording process is performed, the information processing device according to the embodiment records the data representing "the detection result based on the detection signal of the pulse wave sensor" on a storage unit (to be described below) or an external recording medium connected to the information processing device according to the embodiment.

In addition, as the process related to notification of "the detection result based on the detection signal of the pulse wave sensor," for example, a process related to visual notification performed by displaying "the detection result based on the detection signal of the pulse wave sensor" on a display screen of a display device, a process related to auditory notification performed by outputting "the detection result based on the detection signal of the pulse wave sensor" from an audio output device such as a speaker, and a process related to tactile notification performed by vibrating a vibration device in accordance with "the detection result based on the detection signal of the pulse wave sensor" can be exemplified. For example, in a case in which the process related to the visual notification is performed as the notifying process, the information processing device according to the embodiment delivers the data representing "the detection result based on the detection signal of the pulse wave sensor" to a display unit (to be described below) or an external display device connected to the information processing device according to the embodiment and displays "the detection result based on the detection signal of the pulse wave sensor" on the display screen of the display unit (to be described below) or the like.

In addition, for example, the information processing device according to the embodiment can also perform a process of estimating an emotion of the user on the basis of the detection signal of the pulse wave sensor.

For example, the information processing device according to the embodiment estimates an emotion of the user in accordance with one or both of a change in a pulse rate for each predetermined period and a change in the amplitude value of the detection signal for each predetermined period. For example, the information processing device according to the embodiment estimates an emotion of the user by performing pattern matching of a change pattern of one or both of the change in the pulse rate and the change in the amplitude value to a change pattern corresponding to each emotion.

In addition, the information processing device according to the embodiment may estimate an emotion of the user using any technology capable of estimating the emotion of the user.

The information processing device according to the embodiment performs, for example, "the process (the sensor control process) of the foregoing (1)," "the process (the sensor control process) of the foregoing (1) and the process (the estimation process) of the foregoing (2)," "the process (the sensor control process) of the foregoing (1) and the process (the process based on the detection signal of the pulse wave sensor) of the foregoing (3)," or "the process (the sensor control process) of the foregoing (1), the process (the estimation process) of the foregoing (2), and the process (the process based on the detection signal of the pulse wave sensor) of the foregoing (3)" as the process related to the information processing method according to the embodiment.

Also, "the process (the sensor control process) of the foregoing (1)," "the process (the sensor control process) of the foregoing (1) and the process (the estimation process) of the foregoing (2)," "the process (the sensor control process) of the foregoing (1) and the process (the process based on the detection signal of the pulse wave sensor) of the foregoing (3)," and "the process (the sensor control process) of the foregoing (1), the process (the estimation process) of the foregoing (2), and the process (the process based on the detection signal of the pulse wave sensor) of the foregoing (3)" are processes into which the process related to the information processing method according to the embodiment is classified for convenience. Accordingly, in the process related to the information processing method according to the embodiment, for example, "the process (the sensor control process) of the foregoing (1) and the process (the estimation process) of the foregoing (2)," "the process (the sensor control process) of the foregoing (1) and the process (the process based on the detection signal of the pulse wave sensor) of the foregoing (3)," or "the process (the sensor control process) of the foregoing (1), the process (the estimation process) of the foregoing (2), and the process (the process based on the detection signal of the pulse wave sensor) of the foregoing (3)" can be ascertain as one process.

In addition, in the process related to the information processing method according to the embodiment, for example, "the process (the sensor control process) of the foregoing (1)," "the process (the sensor control process) of the foregoing (1) and the process (the estimation process) of the foregoing (2)," "the process (the sensor control process) of the foregoing (1) and the process (the process based on the detection signal of the pulse wave sensor) of the foregoing (3)," or "the process (the sensor control process) of the foregoing (1), the process (the estimation process) of the foregoing (2), and the process (the process based on the detection signal of the pulse wave sensor) of the foregoing (3)" can be ascertained as two or more processes (in accordance with any classifying method).

[3] Specific Example of Process Related to Information Processing Method According to Embodiment Next, a specific example of the process related to the information processing method according to the above-described embodiment will be described. Hereinafter, a case in which the information processing device according to the embodiment performs the process (the sensor control process) of the foregoing (1) and the process (the estimation process) of the foregoing (2) as the process related to the information processing method according to the embodiment will be exemplified.

Figure 2:
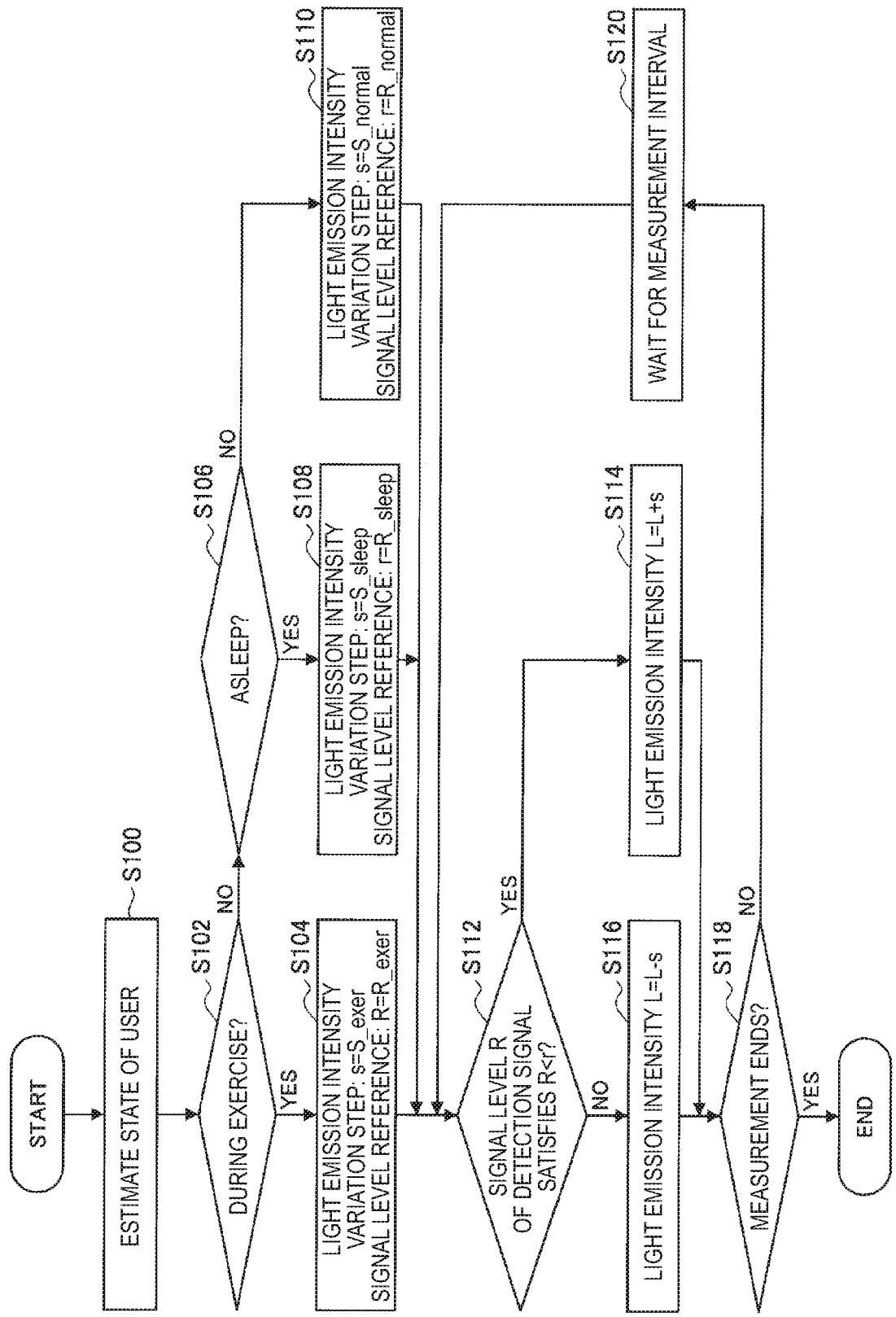
FIG. 2 is a flowchart illustrating an example of a process related to the information processing method according to the embodiment.

FIG. 2 is a flowchart illustrating an example of a process related to the information processing method according to the embodiment. Here, a process of step S100 illustrated in FIG. 2 is equivalent to an example of the process (the estimation process) of the foregoing (2) and processes of steps S102 to S120 illustrated in FIG. 2 are equivalent to an example of the sensor control process related to the third example described in the foregoing (1-3).

The information processing device according to the embodiment estimates the state of the user (S100). For example, the information processing device according to the embodiment estimates the state of the user on the basis of one or two or more of "the behavior taken by the user," "the environment in which the user is located," and "the detection result based on the detection signal of the pulse wave sensor."

In FIG. 2, a case in which the information processing device according to the embodiment estimates three states, "asleep," "physically active," and "daily activities (a state other than asleep and physically active)," as the state of the user will be exemplified.

The information processing device according to the embodiment determines whether the state of the user estimated in step S100 is "physically active (described as "during exercise" in FIG. 2)" (S102).

In a case in which it is determined in step S102 that the state of the user is "physically active," the information processing device according to the embodiment sets a variation amount s of the light emission intensity (described as "light emission intensity variation step" in FIG. 2) to s=S_exer and sets a threshold R (described in "signal level reference" in FIG. 2) to R=R_exer (S104). Then, the information processing device according to the embodiment performs a process subsequent to step S112 to be described below.

Here, the information processing device according to the embodiment specifies S_exer and R_exer, for example, by referring to the table (or the database) in which the state of the user is associated with the variation amount of the light emission intensity and the threshold.

In a case in which it is determined in step S102 that the state of the user is not "physically active," the information processing device according to the embodiment determines whether the state of the use estimated in step S100 is "asleep" (S106).

In a case in which it is determined in step S106 that the state of the user is "asleep," the information processing device according to the embodiment sets the variation amount s of the light emission intensity to s=S_sleep and sets the threshold R to R=R_sleep (S108). Then, the information processing device according to the embodiment performs the process subsequent to step S112 to be described below.

Here, the information processing device according to the embodiment specifies S_sleep and R_sleep, for example, by referring to the table (or the database) in which the state of the user is associated with the variation amount of the light emission intensity and the threshold.

In a case in which it is determined in step S106 that the state of the user is not "asleep," the information processing device according to the embodiment sets the variation amount s of the light emission intensity to s=S_normal and sets the threshold R to R=R_normal (S110). Then, the information processing device according to the embodiment performs the process subsequent to step S112 to be described below.

Here, the information processing device according to the embodiment specifies S_sleep and R_sleep, for example, by referring to the table (or the database) in which the state of the user is associated with the variation amount of the light emission intensity and the threshold.

As "the foregoing S_exer, S_sleep, and S_normal" and "the foregoing R_exer, R_sleep, and R_normal," for example, values for realizing the following cases can be exemplified:
  in the case in which the state of the user is "physically active": a threshold (for example, corresponding to an amplitude reference of a pulse wave component) is increased and the variation amount of the light emission intensity (for example, a change in the amount of emitted light) is increased;
  in the case in which the state of the user is "daily activities": the threshold is not changed and the variation amount of the light emission intensity is not changed from the reference either; and
  in the case in which the state of the user is "asleep": the threshold is decreased and the variation amount of the light emission intensity is also decreased.

Specifically, as a relation among the foregoing S_exer, S_sleep, and S_normal, for example, "S_sleep<S_normal<S_exer" can be exemplified. In addition, as a relation among the foregoing R_exer, R_sleep, and R_normal, for example, "R_sleep<R_normal<R_exer" can be exemplified.

Here, the foregoing S_exer, S_sleep, and S_normal are set, for example, on the basis of measurement data or the like of a subject in each state of the user. In addition, the foregoing S_exer, S_sleep, and S_normal may also be set on the basis of a user manipulation or the like. In addition, the foregoing S_exer, S_sleep, and S_normal are set for each user to, for example, values corresponding to the user authenticated in accordance with any authentication method such as vein authentication, face authentication, or password authentication.

In addition, the foregoing R_exer, R_sleep, and R_normal are set, for example, on the basis of measurement data or the like of a subject in each state of the user. In addition, the foregoing R_exer, R_sleep, and R_normal may also be set on the basis of a user manipulation or the like. In addition, the foregoing R_exer, R_sleep, and R_normal are set for each user to, for example, values corresponding to the user authenticated in accordance with any authentication method such as vein authentication, face authentication, or password authentication.

When one of steps S104, S108, and S110 is performed, the information processing device according to the embodiment determines whether the signal level R of the detection signal of the pulse wave sensor is less than r set in one of steps S104, S108, and S110 (S112). Also, for example, the information processing device according to the embodiment may determine whether the signal level R is equal to or less than r. Here, as the signal level R in step S112, for example, an absolute value of the amplitude value of the detection signal of the pulse wave sensor can be exemplified.

In a case in which it is determined in step S112 that the signal level R is less than r, the information processing device according to the embodiment performs control on the basis of s set in one of steps S104, S108, and S110 such that the light emission intensity increases (S114).

In addition, in a case in which it is determined in step S112 that the signal level R is not less than r, the information processing device according to the embodiment performs control on the basis of s set in one of steps S104, S108, and S110 such that the light emission intensity decreases (S116).

When one process of steps S114 and S116 is performed, the information processing device according to the embodiment determines whether the measurement by the pulse wave sensor ends (S118).

For example, in a case in which a manipulation signal in accordance with a user manipulation indicating that the measurement ends is detected, the information processing device according to the embodiment determines that the measurement by the pulse wave sensor ends. In addition, the information processing device according to the embodiment can also determine whether the measurement by the pulse wave sensor ends, for example, on the basis of any index such as the number of determinations in step S118, a change in the state of the user, a remaining amount of a battery in the device including the pulse wave sensor, or a time elapsed after start of the measurement of the pulse wave.

In a case in which it is determined in step S118 that the measurement by the pulse wave sensor does not end, the information processing device according to the embodiment waits for a set measurement interval (S120) and repeats the process from step S112. Here, the measurement interval may be a fixed time interval which is set in advance or may be a variable time interval which can be varied on the basis of a user manipulation or the like.

In addition, in a case in which it is determined in step S118 that the measurement by the pulse wave sensor ends, the information processing device according to the embodiment ends the process related to the information processing method according to the embodiment illustrated in FIG. 2.

The information processing device according to the embodiment performs, for example, the process illustrated in FIG. 2 as the process related to the information processing method according to the embodiment.

Through the process illustrated in FIG. 2, the light emission intensity of the light source included in the pulse wave sensor is controlled on the basis of the state of the user. Accordingly, by performing the process illustrated in FIG. 2, the information processing device according to the embodiment can achieve compatibility between the stable detection of the pulse wave by the pulse wave sensor and the reduction in the power consumption in the pulse wave sensor.

Also, the process related to the information processing method according to the embodiment is not limited to the example illustrated in FIG. 2.

For example, in FIG. 2, the example in which the light emission intensity is raised or lowered in the same variation step (a variation amount) has been described, but variation step widths that are asymmetric may be set. In addition, for example, the information processing device according to the embodiment may change the variation step widths after the light emission intensity is changed and then changed a given number of times or after a given period has elapsed.

In addition, in a case in which the information processing device according to the embodiment controls a light emission interval in a pulse form through PWM control or the like, for example, the information processing device according to the embodiment may acquire the state of the user at each light emission timing and perform control to an amount of emitted light in accordance with the acquired state. In addition, for example, the information processing device according to the embodiment may change control content using a change in the state of the user as a trigger.

In addition, for example, the information processing device according to the embodiment can also acquire surrounding light amount information indicating an amount of light around the device that includes the pulse wave sensor and obtained from an illuminance sensor included in the device including the pulse wave sensor and control the light emission intensity of the light source of the pulse wave sensor further on the basis of the surrounding light amount information.

As a specific example, in a case in which the amount of surrounding light indicated by the surrounding light amount information is greater than a threshold related to a set amount of light (or the amount of surrounding light is equal to or greater than the threshold related to the amount of light), the information processing device according to the embodiment controls the light emission intensity of the light source of the pulse wave sensor such that the amount of emitted light is further increased to be greater than the light emission intensity. In addition, in a case in which the amount of surrounding light indicated by the surrounding light amount information is equal to or less than the threshold related to the set amount of light (or the amount of surrounding light is equal to or less than the threshold related to the amount of light), the information processing device according to the embodiment controls the light emission intensity of the light source of the pulse wave sensor such that the amount of emitted light is further decreased to be less than the light emission intensity.

For example, as described above, the information processing device according to the embodiment controls the light emission intensity of the light source of the pulse wave sensor further on the basis of the surrounding light amount information. In this way, the decrease in a change ratio of the light emission control is realized in a case in which a change in the amount of surrounding light is small, and the increase in the change in the light emission control is realized in an environment in which the amount of surrounding light is dynamically changed. Accordingly, for example, as described above, by controlling the light emission intensity of the light source of the pulse wave sensor further on the basis of the surrounding light amount information, the information processing device according to the embodiment can achieve compatibility between the stable detection of the pulse wave by the pulse wave sensor and a more decrease in the power consumption in the pulse wave sensor.

In addition, for example, in a case in which information (data) indicating the state of the user estimated in an external device is acquired, the information processing device according to the embodiment may not perform the process of step S100.

In addition, for example, the information processing device according to the embodiment can also further perform the process (the process based on the detection signal of the pulse wave sensor) of the foregoing (3).

(Information Processing Device According to Embodiment)

Next, an example of a configuration of the information processing device according to the embodiment capable of performing the process related to the information processing method according to the above-described embodiment will be described.

Hereinafter, a case in which the information processing device according to the embodiment is a device including the pulse wave sensor will be exemplified. Also, the information processing device according to the embodiment may be a devices separated from a device including the pulse wave sensor, such as a wearable device including the pulse wave sensor. In a case in which the information processing device according to the embodiment is a device separated from the device including the pulse wave sensor, the information processing device according to the embodiment controls the light emission intensity or the like of the light source included in the pulse wave sensor by transmitting a control signal to the device including the pulse wave sensor.

Figure 3:
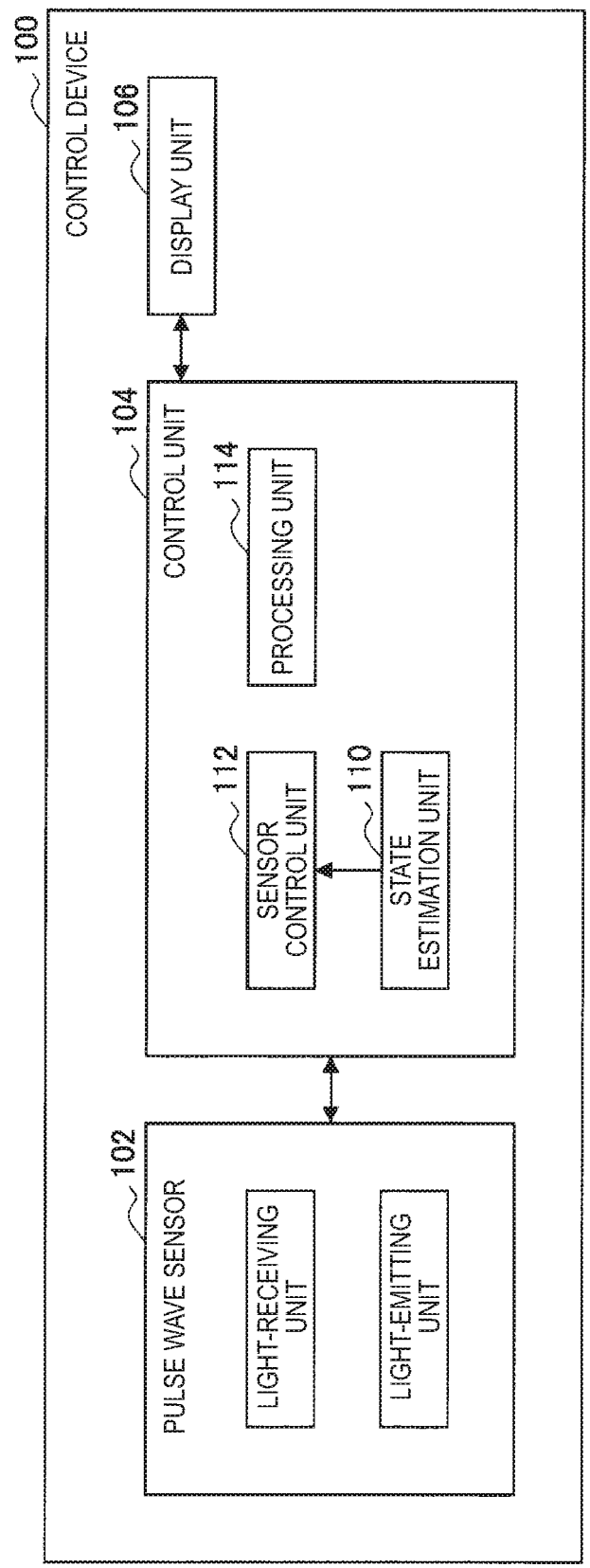
FIG. 3 is a block diagram illustrating an example of a configuration of an information processing device according to the embodiment.

FIG. 3 is a block diagram illustrating an example of the configuration of an information processing device 100 according to the embodiment. The information processing device 100 includes, for example, a pulse wave sensor 102, a control unit 104, and a display unit 106.

In addition, the information processing device 100 may include, for example, a read-only memory (ROM) (not illustrated), a random access memory (RAM) (not illustrated), a storage unit (not illustrated), a communication unit (not illustrated), and a manipulation unit (not illustrated) which can be manipulated by the user). In the information processing device 100, for example, the foregoing constituent elements are connected by a bus serving as a data transmission path.

The ROM (not illustrated) stores a program and control data such as arithmetic parameters which are used by the control unit 104. The RAM (not illustrated) temporarily stores a program or the like which is executed by the control unit 104.

The storage unit (not illustrated) is storage means included in the information processing device 100 and stores, for example, various kinds of data such as various applications or data related to the information processing method according to the embodiment, such as the table in which the state of the user is associated with the variation amount of the light emission intensity. Here, as the storage unit (not illustrated), for example, a magnetic recording medium such as a hard disk or a nonvolatile memory such as a flash memory can be exemplified. In addition, the storage unit (not illustrated) may be detachably mounted on the information processing device 100.

As the communication unit (not illustrated), for example, a communication interface to be described below can be exemplified. In addition, as the manipulation unit (not illustrated), for example, a manipulation input device to be described below can be exemplified.

[Example of Hardware Configuration of Information Processing Device 100]

Figure 4:
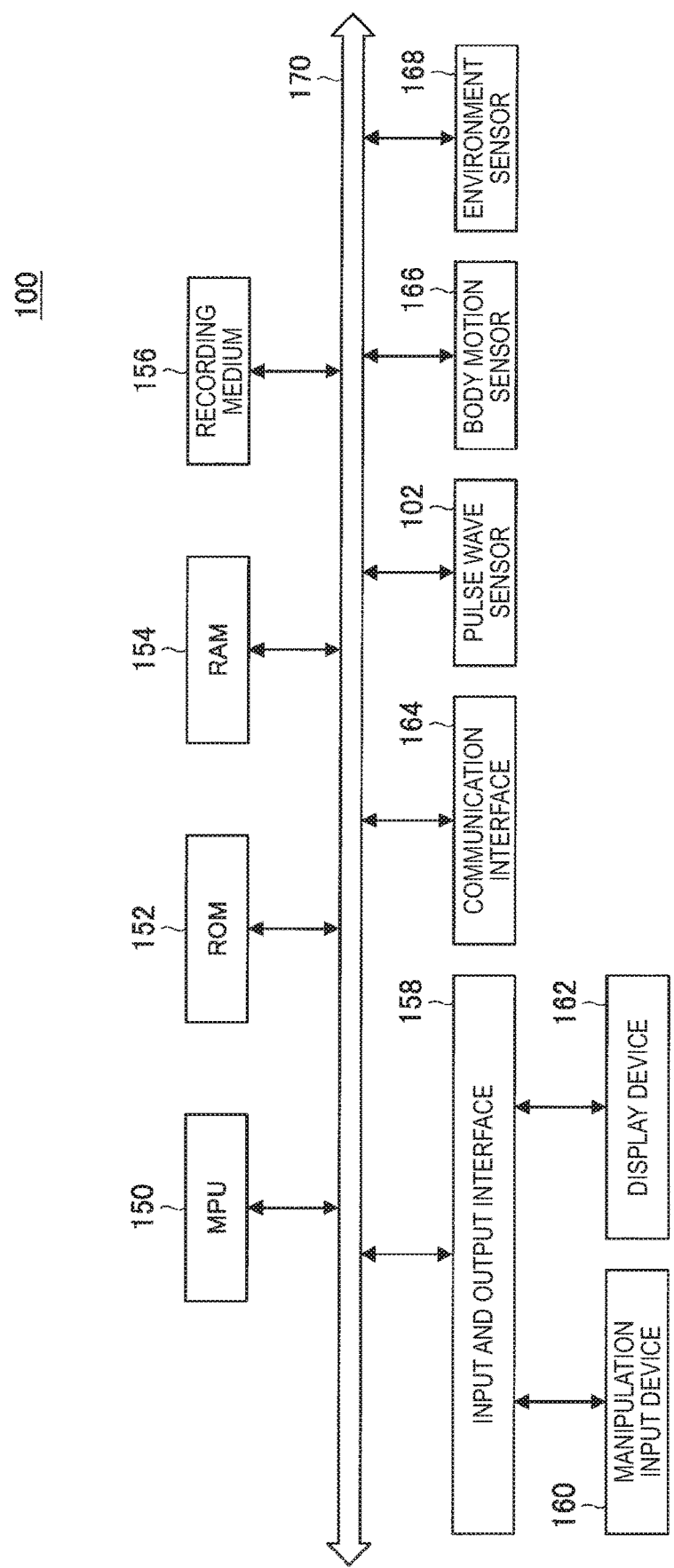
FIG. 4 is an explanatory diagram illustrating an example of a hardware configuration of the information processing device according to the embodiment.

FIG. 4 is an explanatory diagram illustrating an example of a hardware configuration of the information processing device 100 according to the embodiment. FIG. 4 illustrates an example of the hardware configuration in a case in which the information processing device 100 is a wearable device including the pulse wave sensor.

The information processing device 100 includes, for example, an MPU 150, a ROM 152, a RAM 154, a recording medium 156, an input and output interface 158, a manipulation input device 160, a display device 162, a communication interface 164, a pulse wave sensor 102, a body motion sensor 166, and an environment sensor 168. In addition, in the information processing device 100, for example, the foregoing constituent elements are connected by a bus 170 serving as a data transmission path.

For example, the MPU 150 is configured with one or two or more processors or various processing circuits configured with arithmetic circuits such as MPUs and function as the control unit 104 that controls the entire information processing device 100. In addition, for example, the MPU 150 serves as a state estimation unit 110, a sensor control unit 112, and a processing unit 114 to be described below in the information processing device 100. Also, one or two or more of the state estimation unit 110, the sensor control unit 112, and the processing unit 114 may be configured with a dedicated (or general) circuit (for example, a processor separated from the MPU 150) capable of realizing a process of each of the state estimation unit 110, the sensor control unit 112, and the processing unit 114 to be described below.

The ROM 152 stores a program or control data such as arithmetic parameters which are used by the MPU 150. The RAM 154 temporarily stores, for example, a program which is executed by the MPU 150.

The recording medium 156 function as a storage unit (not illustrated) and stores, for example, various kinds of data such as various applications or data related to the information processing method according to the embodiment, such as the table in which the state of the user is associated with the variation amount of the light emission intensity. Here, as the recording medium 156, for example, a magnetic recording medium such as a hard disk or a nonvolatile memory such as a flash memory can be exemplified. In addition, the recording medium 156 may be detachably mounted on the information processing device 100.

The input and output interface 158 connects, for example, the manipulation input device 160 or the display device 162. The manipulation input device 160 functions as a manipulation unit (not illustrated) and the display device 162 functions as the display unit 106. Here, as the input and output interface 158, for example, a Universal Serial Bus (USB) terminal, a Digital Visual Interface (DVI) terminal, a High-Definition Multimedia Interface (HDMI) (registered trademark) terminal, and various processing circuits can be exemplified.

For example, the manipulation input device 160 is included on the information processing device 100 and is connected to the input and output interface 158 inside the information processing device 100. As the manipulation input device 160, for example, a button, a direction key, a rotational selector such as a jog dial, or a combination thereof can be exemplified.

The display device 162 is display means included in the information processing device 100 and displays various screens such as a screen on which "the detection result based on the detection signal of the pulse wave sensor" such as a detected pulse rate is displayed on the display screen.

For example, the display device 162 is included on the information processing device 100 and is connected to the input and output interface 158 inside the information processing device 100. As the display device 162, for example, a liquid crystal display and an organic electro-luminescence (EL) display (or also called an organic light emitting diode (OLED) display) can be exemplified.

Also, it is needless to say that the input and output interface 158 can also be connected to an external manipulation input device (for example, a keyboard or a mouse) of the information processing device 100 or an external device such as an external display device. In addition, the display device 162 may be a device in which a display operation and a user manipulation can be performed, such as a touch panel.

The communication interface 164 is communication means included in the information processing device 100 and functions as a communication unit (not illustrated) that performs wireless or wired communication with an external device such as a server via a network (or directly). Here, as the communication interface 164, for example, a communication antenna and a radio frequency (RF) circuit (for wireless communication), an IEEE 802.15.1 port and a transmission and reception circuit (for wireless communication), and an IEEE 802.11 port and a transmission and reception circuit (for wireless communication), or a local area network (LAN) terminal and a transmission and reception circuit (for wired communication) can be exemplified.

The pulse wave sensor 102 is a sensor that detects a pulse wave in accordance with any scheme capable of detecting a pulse wave, such as a photoelectric pulse wave scheme. The pulse wave sensor 102 includes, for example, a light-emitting unit that emits light for detecting a pulse wave and a reception unit that generates a signal (a detection signal of the pulse wave) in accordance with the received light.

The light-emitting unit of the pulse wave sensor 102 includes one or two or more light sources such as light-emitting diodes. In addition, the light-receiving unit of the pulse wave sensor 102 includes, for example, a photodiode, an amplification circuit, a filter circuit, and an analog-to-digital converter.

For example, in a case in which the pulse wave sensor 102 has the configuration illustrated in FIG. 1, light emitted from the light-emitting unit is reflected in accordance with an increase or decrease in an amount of blood in association with beats of the heart via a skin of a living tissue and the reflected light is received by the light-receiving unit.

The filter circuit of the light-receiving unit removes a DC component of a signal obtained by receiving the light in the photodiode. Here, as the filter circuit, for example, a capacitor performing DC cut by performing AC coupling or a highpass filter passing a signal with a predetermined frequency or more such as a signal of 0.5 [Hz] or more can be exemplified.

In addition, the filter circuit of the light-receiving unit may be configured to perform filtering on an analog signal or may be configured to performing filtering on a digital signal quantized by converting the analog signal by the analog-to-digital converter.

Also, for example, in a case in which the light source included in the light-emitting unit of the pulse wave sensor 102 is driven through PWM control, a value obtained by subtracting a signal level at the time of emission of the light from the light source and a signal level at the time of non-emission of the light from the light source can also be set as a detection signal of a pulse wave in the light-receiving unit of the pulse wave sensor 102.

The body motion sensor 166 is, for example, a sensor related to sensing of a motion of the information processing device 100. As the body motion sensor 166, for example, one or two or more sensors capable of detecting a motion, such as an acceleration sensor or a gyro sensor, can be exemplified.

Also, the body motion sensor 166 is not limited to the foregoing example. For example, the body motion sensor 166 may be any sensor capable of obtaining any sensing result which can be used to estimate the state of the user, such as a geomagnetic sensor or an image sensor including an imaging device.

The environment sensor 168 is a sensor related to sensing of an environment in which the information processing device 100 is located. As the environment sensor 168, for example, an illuminance sensor that senses an amount of light around the information processing device 100 can be exemplified. In addition, the environment sensor 169 may be, for example, any sensor capable of sensing an environment in which the information processing device 100 is located, such as a sound collection device that senses a sound around the information processing device 100.

For example, in the configuration illustrated in FIG. 4, the information processing device 100 performs the process related to the information processing method according to the embodiment. Also, a hardware configuration of the information processing device 100 according to the embodiment is not limited to the configuration illustrated in FIG. 4.

For example, in a case in which the information processing device 100 performs communication with an external device or the like via a connected external communication device or is configured to perform a process as a standalone device, the communication interface 164 may not be included. In addition, the communication interface 164 may be configured to perform communication with one or two or more external devices in accordance with a plurality of communication schemes.

In addition, the information processing device 100 can also be configured not to include, for example, the recording medium 156, the manipulation input device 160, or the display device 162.

In addition, for example, in a case in which the information processing device 100 controls a pulse wave sensor included in an external device, the information processing device 100 can be configured not to include one or two or more of the pulse wave sensor 102, the body motion sensor 166, and the environment sensor 168.

In addition, for example, the configuration illustrated in FIG. 4 (or a configuration according to a modification example) may be realized by one or two or more ICs.

Referring back to FIG. 3, an example of the configuration of the information processing device 100 will be described. The pulse wave sensor 102 detects a pulse wave in accordance with any scheme, such as a photoelectric pulse wave scheme, capable of detecting the pulse wave.

The control unit 104 is configured with, for example, an MPU and serves to control the entire information processing device 100. In addition, the control unit 104 includes, for example, the state estimation unit 110, the sensor control unit 112, and the processing unit 114 and serves to lead the process related to the information processing method according to the embodiment.

The state estimation unit 110 serves to lead the process (the estimation process) of the foregoing (2) and estimates the state of the user. For example, the state estimation unit 110 estimates the state of the user on the basis of one or two or more of "the behavior taken by the user," "the environment in which the user is located," and "the detection result based on the detection signal of the pulse wave sensor."

The sensor control unit 112 serves to lead the process (the sensor control process) of the foregoing (1) and controls the light emission intensity of the light source included in the pulse wave sensor 102 on the basis of the state of the user who is the detection target of the pulse wave sensor 102. For example, the sensor control unit 112 uses the state of the user estimated by the state estimation unit 110 or the state of the user estimated by an external device in the process.

More specifically, the sensor control unit 112 controls the light emission intensity of the light source included in the pulse wave sensor 102, for example, by performing the sensor control process related to the first example described in the foregoing (1-1) to the sensor control process related to the third example described in the foregoing (1-3).

In addition, the sensor control unit 112 may further control the light reception operation in the light-receiving device included in the pulse wave sensor.

The processing unit 114 serves to lead the process (the process based on the detection signal of the pulse wave sensor) of the foregoing (3) and performs the process based on the detection signal of the pulse wave sensor 102. For example, on the basis of the detection signal of the pulse wave sensor 102, the processing unit 114 performs one or two or more processes which can be performed on the basis of the detection signal of the pulse wave sensor 102, such as the process of obtaining "the detection result based on the detection signal of the pulse wave sensor" and the process of notifying of "the detection result based on the detection signal of the pulse wave sensor," as described above.

For example, the control unit 104 includes the state estimation unit 110, the sensor control unit 112, and the processing unit 114, and thus performs the process related to the information processing method according to the embodiment (for example, "the process (the sensor control process) of the foregoing (1), the process (the estimation process) of the foregoing (2), and the process (the process based on the detection signal of the pulse wave sensor) of the foregoing (3)").

The display unit 106 displays various screens, such as a screen on which "the detection result based on the detection signal of the pulse wave sensor" such as a detected pulse rate is displayed, on the display screen. The screen on which "the detection result based on the detection signal of the pulse wave sensor" is displayed is displayed through, for example, a process of notifying of "the detection result based on the detection signal of the pulse wave sensor" in the processing unit 114.

For example, in the configuration illustrated in FIG. 3, the information processing device 100 performs the process related to the information processing method according to the embodiment (for example, "the process (the sensor control process) of the foregoing (1), the process (the estimation process) of the foregoing (2), and the process (the process based on the detection signal of the pulse wave sensor) of the foregoing (3)").

Accordingly, for example, in the configuration illustrated in FIG. 3, the information processing device 100 can achieve compatibility between the stable detection of the pulse wave by the pulse wave sensor and the reduction in the power consumption in the pulse wave sensor.

In addition, for example, in the configuration illustrated in FIG. 3, the information processing device 100 can obtain the effects obtained by performing the process related to the information processing method according to the above-described embodiment.

Also, a configuration of the information processing device according to the embodiment is not limited to the configuration illustrated in FIG. 3.

For example, the information processing device according to the embodiment may be configured not to include one or both of the state estimation unit 110 and the processing unit 114 illustrated in FIG. 3.

Even in a case in which the information processing device has the configuration in which one or both of the state estimation unit 110 and the processing unit 114 illustrated in FIG. 3 are not included, the information processing device according to the embodiment can perform the process (the sensor control process) of the foregoing (1). Accordingly, even in the case in which the information processing device has the configuration in which one or both of the state estimation unit 110 and the processing unit 114 illustrated in FIG. 3 are not included, the information processing device according to the embodiment can achieve compatibility between the stable detection of the pulse wave by the pulse wave sensor and the reduction in the power consumption in the pulse wave sensor.

In addition, the information processing device according to the embodiment can include one or two or more of the state estimation unit 110, the sensor control unit 112, and the processing unit 114 illustrated in FIG. 3 separately from the control unit 104 (for example, these units are realized by another processing circuit).

In addition, for example, in a case in which the information processing device according to the embodiment controls a pulse wave sensor included in an external device, the information processing device according to the embodiment may not include the pulse wave sensor 102 illustrated in FIG. 3. In addition, the information processing device according to the embodiment can also have a configuration in which the display unit 106 illustrated in FIG. 3 is not included.

Even in a case in which the information processing device has a configuration in which one or both of the pulse wave sensor 102 and the display unit 106 illustrated in FIG. 3 are not included, the information processing device according to the embodiment can perform the process related to the information processing method according to the embodiment (for example, "the process (the sensor control process) of the foregoing (1), the process (the estimation process) of the foregoing (2), and the process (the process based on the detection signal of the pulse wave sensor) of the foregoing (3)"). Accordingly, even in the case in which the information processing device has the configuration in which one or both of the pulse wave sensor 102 and the display unit 106 are not included, the information processing device according to the embodiment can obtain the same advantage as the information processing device 100 illustrated in FIG. 3 (or the information processing device according to the above-described modification).

In addition, as described above, "the process (the sensor control process) of the foregoing (1)," "the process (the sensor control process) of the foregoing (1) and the process (the estimation process) of the foregoing (2)," "the process (the sensor control process) of the foregoing (1) and the process (the process based on the detection signal of the pulse wave sensor) of the foregoing (3)," or "the process (the sensor control process) of the foregoing (1), the process (the estimation process) of the foregoing (2), and the process (the process based on the detection signal of the pulse wave sensor) of the foregoing (3)" are processes into which the process related to the information processing method according to the embodiment is classified for convenience. Accordingly, a configuration for realizing the process related to the information processing method according to the embodiment is not limited to the state estimation unit 110, the sensor control unit 112, and the processing unit 114 illustrated in FIG. 3. The information processing device can have a configuration in accordance with a method of classifying the process related to the information processing method according to the embodiment.

The information processing device has been exemplified according to the embodiment, but the invention is not limited to the form. For example, the embodiment can be applied to various devices capable of performing the process related to the information processing method according to the embodiment, such as a device including a pulse wave sensor such as a wearable device including a pulse wave sensor, a computer such as a personal computer (PC) or a server, a communication device such as a tablet device, a mobile phone, or a smartphone, and a vehicle such as an automobile. In addition, for example, the embodiment can also be applied to a processing IC which can be embedded in the foregoing device.

In addition, the information processing device according to the embodiment may be applied to, for example, a system formed by a plurality of devices on the premise of connection to a network (or communication between devices) such as cloud computing. That is, the information processing device according to the above-described embodiment can also be realized as, for example, an information processing system in which the process related to the information processing method according to the embodiment is performed by the plurality of devices. As an example of the information processing system in which the process related to the information processing method according to the embodiment is performed by the plurality of devices, for example, a system in which "the process (the sensor control process) of the foregoing (1), the process (the estimation process) of the foregoing (2), and the process (the process based on the detection signal of the pulse wave sensor) of the foregoing (3)" is performed in cooperation of the plurality of devices included in the information processing system can be exemplified.

(Program According to Embodiment)

By causing a processor or the like of a computer to execute a program causing the computer to function as the information processing method according to the embodiment (for example, a program capable of performing the process related to the information processing method according to the embodiment such as "the process (the sensor control process) of the foregoing (1)," "the process (the sensor control process) of the foregoing (1) and the process (the estimation process) of the foregoing (2)," "the process (the sensor control process) of the foregoing (1) and the process (the process based on the detection signal of the pulse wave sensor) of the foregoing (3)," or "the process (the sensor control process) of the foregoing (1), the process (the estimation process) of the foregoing (2), and the process (the process based on the detection signal of the pulse wave sensor) of the foregoing (3)"), the computer can achieve compatibility between the stable detection of a pulse wave by the pulse wave sensor and the reduction in the power consumption in the pulse wave sensor.

Moreover, when a program that causes a computer to function as the information processing apparatus according to the present embodiment is executed by a processor or the like in the computer, it is possible to provide an effect provided by the processing related to the information processing method according to the present embodiment described above.

The preferred embodiment of the present disclosure has been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, it has been illustrated above that a program (computer program) that causes a computer to function as the information processing apparatus according to the present embodiment is provided, but the present embodiment can further provide a recording medium in which the above-described program is stored together.

The above-described configurations express examples of the present embodiment and, of course, pertain to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
An information processing device including:
a sensor control unit configured to control a light emission intensity of a light source included in a pulse wave sensor on the basis of a state of a user who is a detection target of the pulse wave sensor.

(2)
The information processing device according to (1),
in which the pulse wave sensor includes the one light source, and
the sensor control unit controls the light emission intensity of the one light source.

(3)
The information processing device according to (1),
in which the pulse wave sensor includes a plurality of the light sources, and
the sensor control unit controls the light emission intensities of the plurality of light sources.

(4)
The information processing device according to (3),
in which the pulse wave sensor includes the plurality of light sources that emit different colors of light, and
the sensor control unit controls the light emission intensities of the plurality of light sources that emit the different colors of light.

(5)
The information processing device according to any one of (1) to (4),
in which the sensor control unit controls the light emission intensity of the light source on the basis of a variation amount of the light emission intensity corresponding to the state of the user and a comparison result of an amplitude value of a detection signal of the pulse wave sensor and a predetermined threshold.

(6)
The information processing device according to (5),
in which the predetermined threshold is a value corresponding to the state of the user.

(7)
The information processing device according to any one of (1) to (4),
in which the sensor control unit controls the light emission intensity of the light source on the basis of a predetermined variation amount of the light emission intensity and a comparison result of an amplitude value of a detection signal of the pulse wave sensor and a threshold corresponding to the state of the user.

(8)
Any one of (5) to (7),
in which the sensor control unit
performs control on the basis of the variation amount such that the light emission intensity decreases in a case in which the amplitude value of the detection signal of the pulse wave sensor is greater than the threshold and performs control on the basis of the variation amount such that the light emission intensity increases in a case in which the amplitude value is equal to or less than the threshold, or
performs control on the basis of the variation amount such that the light emission intensity decreases in a case in which the amplitude value is equal to or greater than the threshold and performs control on the basis of the variation amount such that the light emission intensity increases in a case in which the amplitude value is less than the threshold.

(9)
The information processing device according to (8),
in which the sensor control unit controls the light emission intensity such that a manner of changing the light emission intensity in a case in which the light emission intensity decreases is identical to a manner of changing the light emission intensity in a case in which the light emission intensity increases.

(10)
The information processing device according to (8),
in which the sensor control unit controls the light emission intensity such that a manner of changing the light emission intensity in a case in which the light emission intensity decreases is different from a manner of changing the light emission intensity in a case in which the light emission intensity increases.

(11)
The information processing device according to any one of (1) to (10),
in which the sensor control unit further controls a light reception operation in a light-receiving device included in the pulse wave sensor.

(12)
The information processing device according to any one of (1) to (11), further including:
a state estimation unit configured to estimate the state of the user,
in which the sensor control unit controls the light emission intensity on the basis of the state of the user estimated by the state estimation unit.

(13)
The information processing device according to any one of (1) to (12), further including:
a processing unit configured to perform a process based on a detection signal of the pulse wave sensor.

(14)
The information processing device according to any one of (1) to (13), including: the pulse wave sensor.

(15)
An information processing method performed by an information processing device, including:

a step of controlling a light emission intensity of a light source included in a pulse wave sensor on the basis of a state of a user who is a detection target of the pulse wave sensor.

REFERENCE SIGNS LIST 100 information processing device
102 pulse wave sensor
104 control unit
106 display unit
110 state estimation unit
112 sensor control unit
114 processing unit

The invention claimed is:

1. An information processing device, comprising:
a processor configured to:
set a threshold for an amplitude value of a detection signal of a pulse wave sensor based on a current state of a user, wherein the threshold is different for each state of a plurality of states of the user; and
control a light emission intensity of a light source included in the pulse wave sensor based on:
the current state of the user, wherein a detection target of the pulse wave sensor is the user, and
a comparison between the amplitude value of the detection signal of the pulse wave sensor and the set threshold.

2. The information processing device according to claim 1, wherein
the pulse wave sensor includes the light source, and
the processor is configured to control the light emission intensity of the light source.

3. The information processing device according to claim 1, wherein
the pulse wave sensor includes a plurality of light sources including the light source, and
the processor is configured to control light emission intensities of the plurality of light sources.

4. The information processing device according to claim 3, wherein
the pulse wave sensor includes the plurality of light sources that emit different colors of light, and
the processor is configured to control the light emission intensities of the plurality of light sources that emit the different colors of the light.

5. The information processing device according to claim 1, wherein
the processor is configured to control the light emission intensity of the light source based on a variation amount of the light emission intensity corresponding to the state of the user.

6. The information processing device according to claim 5, wherein the processor is further configured to:
decrease the light emission intensity in a case in which the amplitude value of the detection signal of the pulse wave sensor is greater than the set threshold, and increase the light emission intensity in a case in which the amplitude value is equal to or less than the set threshold, or
decrease the light emission intensity in a case in which the amplitude value is equal to or greater than the set threshold, and increase the light emission intensity in a case in which the amplitude value is less than the set threshold.

7. The information processing device according to claim 6, wherein the processor is further configured to control the light emission intensity such that a manner of change of the light emission intensity in a case in which the light emission intensity decreases is identical to a manner of change of the light emission intensity in a case in which the light emission intensity increases.

8. The information processing device according to claim 6, wherein the processor is further configured to control the light emission intensity such that a manner of change of the light emission intensity in a case in which the light emission intensity decreases is different from a manner of change of the light emission intensity in a case in which the light emission intensity increases.

9. The information processing device according to claim 1, wherein
the processor is configured to control the light emission intensity of the light source based on a determined variation amount of the light emission intensity.

10. The information processing device according to claim 1, wherein the processor is further configured to:
control a light reception operation in a light-receiving device included in the pulse wave sensor by operation of the light-receiving device in conjunction with light emission of the light source included in the pulse wave sensor.

11. The information processing device according to claim 1, wherein the processor is further configured to:
estimate the current state of the user; and
control the light emission intensity based on the estimated current state of the user.

12. The information processing device according to claim 1, wherein the processor is further configured to execute a process based on the detection signal of the pulse wave sensor.

13. The information processing device according to claim 1, further comprising
the pulse wave sensor.

14. The information processing device according to claim 1, further comprising a storage device configured to store the plurality of states of the user, wherein each state of the plurality of states of the user is stored in association with a corresponding threshold and a variation amount of the light emission intensity, wherein
in a case where the current state of the user is daily activities state, a first value of the set threshold corresponds to a reference value, and the variation amount of the light emission intensity is not changed,
in a case where the current state of the user is physically active state, the processor is further configured to:
increase the set threshold from the reference value to a second value that corresponds to the physically active state in the storage device; and
control the light emission intensity of the light source included in the pulse wave sensor by a first variation amount that corresponds to the physically active state of the user, and
in a case where the current state of the user is asleep state, the processor is further configured to:
decrease the set threshold from the reference value to a third value that corresponds to the asleep state in the storage device; and
control the light emission intensity of the light source included in the pulse wave sensor by a second variation amount that corresponds to the asleep state of the user.

15. An information processing method, comprising:
in an information processing device:
setting a threshold for an amplitude value of a detection signal of a pulse wave sensor based on a current state of a user, wherein the threshold is different for each state of a plurality of states of the user; and controlling a light emission intensity of a light source included in the pulse wave sensor based on:

the current state of the user, wherein a detection target of the pulse wave sensor is the user, and a comparison between the amplitude value of the detection signal of the pulse wave sensor and the set threshold.

16. An information processing device, comprising:

a processor configured to:

set a threshold for an amplitude value of a detection signal of a pulse wave sensor based on a current state of a user, wherein the threshold is different for each state of a plurality of states of the user;

control a light emission intensity of a light source included in the pulse wave sensor based on:

a variation amount of the light emission intensity corresponding to the current state of the user, wherein a detection target of the pulse wave sensor is the user, and a comparison result of comparison between the amplitude value of the detection signal of the pulse wave sensor and the set threshold;

decrease the light emission intensity in a case where the amplitude value of the detection signal of the pulse wave sensor is greater than the set threshold;

increase the light emission intensity in a case where the amplitude value is one of equal to or less than the set threshold;

decrease the light emission intensity in a case where the amplitude value is one of equal to or greater than the set threshold; and increase the light emission intensity in a case where the amplitude value is less than the set threshold.

* * * * *